US 6,689,911 B2

(12) United States Patent
Kruk et al.

(10) Patent No.: US 6,689,911 B2
(45) Date of Patent: Feb. 10, 2004

(54) PROCESS

(75) Inventors: Henry Kruk, San José, CA (US); John McGinley, San Fransico, CA (US); Sergei Pouhov, Fremont, CA (US); John Vajda, Sunnyvale, CA (US); Allan Wilcox, Mountain View, CA (US); Jörgen Blixt, Södertälje (SE); Ulf Larsson, Åkers Styckebruk (SE)

(73) Assignees: Centaur Pharmaceuticals, Inc., Sunnyvale, CA (US); AstraZeneca AB, Södertalje (SE)

(*) Notice: Subject to any disclaimer, the term of this patent is extended or adjusted under 35 U.S.C. 154(b) by 335 days.

(21) Appl. No.: 09/806,833

(22) PCT Filed: Jan. 4, 2001

(86) PCT No.: PCT/SE01/00008

§ 371 (c)(1),
(2), (4) Date: Apr. 5, 2001

(87) PCT Pub. No.: WO01/51461

PCT Pub. Date: Jul. 19, 2001

(65) Prior Publication Data

US 2003/0069442 A1 Apr. 10, 2003

(30) Foreign Application Priority Data

Jan. 10, 2000 (SE) .............................................. 0000056

(51) Int. Cl.[7] ........................................... C07C 291/04
(52) U.S. Cl. ........................ 564/298; 562/58; 564/299

(58) Field of Search ............................ 562/58; 564/298, 564/299

(56) References Cited

U.S. PATENT DOCUMENTS 5,475,032 A * 12/1995 Carney ....................... 514/576

FOREIGN PATENT DOCUMENTS

| FR | 1437188 | 6/1995 |
|----|---------|--------|
| WO | WO 95 17876 | 7/1995 |

OTHER PUBLICATIONS

Janzen et al; Spin Trapping Chemistry of Sodium 2–Sulfonatophenyl t–Butyl Nitrone (Na+2–SPBN–); A Negatively Charged Water–Soluble Spin Trap; Tetrahedron Letters, vol. 35, pp. 3229–3232; 1979.

Hinton et al; "Synthesis and Characterization of Phenyl–Substituted C–Pheny 1–N–tert–butylnitrones and Some of Their Radical Adducts", J. Org. Chem., vol. 57, No. 9; pp. 2646–2651, p 2648, left column; 1992.

* cited by examiner

*Primary Examiner*—Peter O'Sullivan
(74) *Attorney, Agent, or Firm*—Nixon & Vanderhye

(57) ABSTRACT

An integrated process for preparing α-(2,4-disulfophenyl)-N-tert-butylnitrone and its salts is disclosed in which N-tert-butylhydroxylamine acid addition salt is incompletely neutralised so as to leave catalytic amounts of acid and the neutralisation product is condensed with an appropriate aldehyde.

8 Claims, No Drawings

PROCESS

This application is a 317 of PCT/SE01/00008 filed Jan. 4, 2002.

FIELD OF THE INVENTION

This invention relates to a novel process for the preparation of α-(2,4-disulfophenyl)-N-tert-butylnitrone and pharmaceutically acceptable salts thereof. These compounds have previously been disclosed as being useful as medicaments. Such compounds are alternatively named as 4-[(tert-butylimino)methyl]benzene-1,3-disulfonic acid N-oxide derivatives.

BACKGROUND OF THE INVENTION

U.S. Pat. No. 5,488,145 discloses α-(2,4-disulfophenyl)-N-tert-butylnitrone, pharmaceutically acceptable salts thereof and related pharmaceutical compositions. U.S. Pat. No. 5,475,032 discloses the use of such compositions in the treatment of stroke and of progressive central nervous system function loss conditions. And U.S. Pat. No. 5,508,305 discloses the use of such compositions for ameliorating the side effects caused by oxidative damage resulting from antineoplastic disease treatment. Similar disclosures are also made in WO 95/17876. U.S. Pat. No. 5,780,510 discloses the use of these same compounds in the treatment of concussion.

Various methods are available for the synthesis of nitrones. The most often used method involves the usually uncatalysed condensation reaction of a hydroxylamine derivative with an aldehyde or ketone (J. S. Roberts in D. H. R. Barton and W. D. Ollis, *Comprehensive Organic Chemistry*, Volume 2, pages 500–504, Pergamon Press, 1979; R. D. Hinton and E. G. Janzen, *J. Org. Chem.*, 1992, 57, 2646–2651). The utility of this reaction is impaired by its susceptibility to steric hindrance, slow reaction rates, and, in certain cases, by the relative inaccessibility and/or instability of the hydroxylamine starting material. The latter problems can sometimes be overcome by in situ generation of the required hydroxylamine by reduction of a more readily available compound such as the corresponding nitro derivative. This general methodology is employed in the above-described patents where the preparation of α-(2,4-disulfophenyl)-N-tert-butylnitrone is described as involving the reaction of 4-formyl-1,3-benzenesulfonic acid with N-tert-butylhydroxylamine in refluxing methanol for approximately 18 hours.

α-(2-Sulfophenyl)-N-tert-butylnitrone has been prepared by reaction of 2-formylbenzenesulfonic acid sodium salt with N-tert-butylhydroxylamine in refluxing ethanol for 2 days (E. G. Janzen and R. V. Shetty, *Tetrahedron Letters*, 1979, 3229–3232).

A modification of this type of methodology for the manufacture of α-phenyl-N-methylnitrone has been described in French Patent 1,437,188 to E.I. DuPont de Nemours and Co.

We now disclose a novel process that possesses significant advantages for the preparation of α-(2,4-disulfophenyl)-N-tert-butylnitrone and salts thereof and is also particularly suited to large scale production.

DISCLOSURE OF THE INVENTION

This invention provides a process for the preparation of a compound of general formula (I)

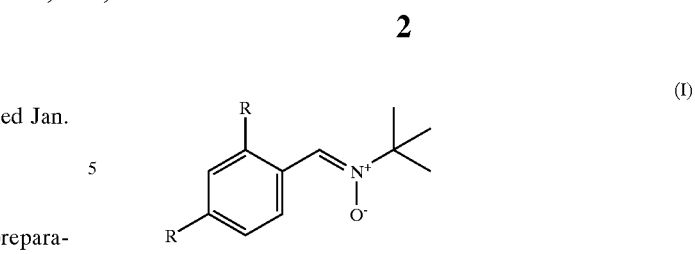

wherein each R independently represents $SO_3H$ or a salt thereof.

This process involves reaction of an aldehyde of general formula (II)

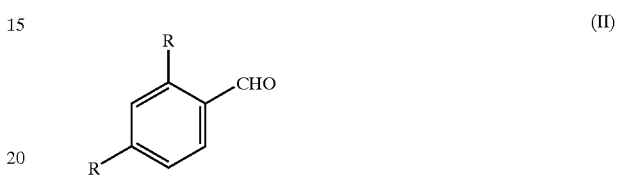

wherein R is as defined above, with freshly prepared N-tert-butylhydroxylamine (III)

$(CH_3)_3CNHOH$            (III)

Thus, in one aspect this invention provides an integrated process in which: in a first step, N-tert-butylhydroxylamine (III) free base is prepared by neutralising N-tert-butylhydroxylamine acid addition salt in an organic reaction medium; in a second step the N-tert-butylhydroxylamine free base (III) formed in the first step is reacted under condensation conditions with an aldehyde of general formula (II), thereby forming the nitrone compound of general formula (I); and in a third step the compound (I) is isolated from the condensation reaction mixture.

In a second aspect, this invention provides an improvement in the condensation of N-tert-butylhydroxylamine (III) with an aldehyde of general formula (II) that comprises conducting the condensation in the presence of an acid catalyst.

In a third aspect, said acid catalyst is provided by incomplete neutralisation of the N-tert-butylhydroxylamine acid addition salt used as one of the starting materials.

DETAILED DESCRIPTION OF THE INVENTION

Starting Materials and Products

In this process, an aldehyde of general formula (II) is reacted with freshly generated N-tert-butylhydroxylamine to form an α-(2,4-disulfophenyl)-N-tert-butylnitrone compound of general formula (I). The compounds of formulae (I) and (II) may be acids or they may be salts.

Salts of compounds of formula (1) above may be formed by reacting the free acid (wherein R represents $SO_3H$), or another salt thereof, with two or more equivalents of an appropriate base, using methods that are well known in the art.

The salts of compounds of formulae (I) and (II) referred to above will normally be those formed with pharmaceutically acceptable cations. The cation may be a monovalent material such as sodium, potassium, lithium, ammonium, alkylammonium or diethanolammonium. Alternatively, it may be a polyvalent cation such as calcium, magnesium, aluminium or zinc. It may also be a mixed salt formed with a polyvalent cation in combination with a pharmaceutically acceptable monovalent anion such as halide (for example, chloride), phosphate, sulphate, acetate, citrate or tartrate.

The two R's in those formulas are usually the same. However, they can be independently selected from the possibilities just enumerated.

It is preferred that the two R's in formulae (I) and (II) above be the same and each represents $SO_3^-Na^+$.

N-tert-Butylhydroxylamine is prepared from a commercially available acid addition salt such as N-tert-butylhydroxylammonium chloride as described below in the section entitled "The Premix Step".

The aldehydes of general formula (II) are either commercially available or may be prepared from commercially available materials using methods that are well known in the art. Commercial 4-formyl-1,3-benzenedisulfonic acid disodium salt (II; $R=SO_3^-Na^+$) typically contains small but significant amounts of the corresponding benzyl alcohol and the corresponding benzoic acid derivatives, and of sodium chloride as impurities. It is preferable, but not essential, that such material is purified before use in the process of the present invention.

4-Formyl-1,3-benzenedisulfonic acid disodium salt (II; $R=SO_3^-Na^+$) is typically associated with varying amounts of water. The proportion of such water generally is not critical to the process of the present invention but generally may be taken into account when determining the overall composition of the compound (I)-forming reaction mixture.

The Premix Step

The free base form of N-tert-butylhydroxylamine is relatively unstable, tending in particular to undergo aerial oxidation. This is evidenced by the formation of blue colours, which indicate the presence of the oxidation product, 2-methyl-2-nitrosopropane. The free base of N-tert-butylhydroxylamine cannot therefore be stored as such but should be freshly generated immediately before use. In view of the instability of the free base of N-tert-butylhydroxylamine, it is advisable, particularly for large scale work, to generate the free base in solution and then to use this solution directly in the subsequent reaction rather than attempting to isolate the free base as such.

A preferred reaction for generating the free base of N-tert-butylhydroxylamine involves reacting in solution N-tert-butylhydroxylamine acid addition salt with a base. Typical acid addition salts include the hydrohalide acid addition salts, with the hydrochloride salt being preferred.

Bases include the simple inorganic bases such as the alkali metal hydroxides. However, these bases are less soluble in organic solvents. Thus, a preferred group of bases are those that are soluble in organic solvents and that do not yield water as a product of neutralisation. Such materials include alkali metal alkoxides such a sodium or potassium methoxide, ethoxide, isopropoxide and the like.

Typical solvents for generating the free base include lower alcohols, such as methanol, ethanol, n-propanol and isopropanol, alone, in mixtures or in mixtures with water. Thus, treatment of a solution of commercial N-tert-butylhydroxylamine hydrochloride in methanol with a base such as sodium methoxide yields a methanolic solution of the free base plus sodium chloride.

The precipitated sodium chloride can be removed by filtration, but the solubility of sodium chloride in methanol is such that significant amounts of sodium chloride remain in solution and are thereby carried forward to become a contaminant of the final product, the nitrone of formula (I). The removal of sodium chloride from compounds of formula (I), particularly the compound wherein R represents $SO_3^-Na^+$, is not a trivial exercise since compounds of formula (I) themselves have very appreciable solubility in solvents such as water. Chloride contamination of the final products (I) can be reduced to acceptable levels by washing with water. This is often at the expense of losing very significant amounts of the desired material (I). In an attempt to overcome this problem, a change of solvent form methanol to isopropanol was investigated. Whilst this approach was successful in terms of reducing the carry over of sodium chloride into the final product, this change of solvent had an unacceptably adverse effect on the rate of the reaction of the aldehyde (II) with N-tert-butylhydroxylamine. Using a solvent mixture comprising methanol 10 to 35% v/v; preferably 20 to 30%; and isopropanol, 90 to 65%, preferably 80 to 70%, in a premix solution, which is filtered, provides a suitable compromise in terms of removing sodium chloride without appreciably increasing the reaction time.

As previously noted, however, one can use individual alcohols or other mixtures if optimal salt rejection and product recovery is less critical.

This premix reaction is moderately exothermic. Thus, depending upon the scale of the reaction it can lead to warming of the reaction mixture by as much as 20° C. or more. Agitation can prevent localised heating. Heat can be removed or added as needed to control the reaction temperature into a typical range of about 0° C. up to about 75° C. with mildly elevated temperatures of say 25° C. to 50° C. being most common.

This reaction is typically carried out with agitation at ambient temperature for a time of from about five minutes up to several hours. Preferably the time is at the shorter end of this range such as from about ten minutes to about fifty minutes.

Prior to using the neutralisation product of the premix as a feedstock in the condensation reaction, it is advantageous to filter it to remove as much as possible of any salt by-product of the neutralisation. This filtration is generally carried out at 0° C. to 30° C. although this temperature is not seen to be critical.

While the amount of base used to neutralise the acid addition salt material can be one equivalent of base per equivalent of salt, in practice it is advantageous to use slightly less than one equivalent of base so as to have a minor amount of acid present which then acts as a catalyst for the subsequent condensation reaction. Thus, the amount of base used to form the free base form of N-tert-butylhydroxylamine is from about 0.9 to 1.0 equivalents (basis equivalents of acid addition salt) and preferably from about 0.95 to 1.0 equivalents and especially from about 0.95 to 0.99 equivalents. This provides 0.1 equivalents or less of catalyst, which gives good results.

The Condensation

The next step is the condensation of the N-tert-butylhydroxylamine (III) with the aldehyde (II). This reaction is typically conducted in a batch mode with agitation. It could, if desired, be carried out continuously in a flow reaction system.

In this condensation it is preferred that in general about 1.0 to 1.5 equivalents of N-tert-butylhydroxylamine (III) is used for each equivalent of the aldehyde (II). It is particularly preferred that about 1.05 to 1.3 equivalents of N-tert-butylhydroxylamine (III) is used.

The condensation is carried out in solution, using a suitable inert solvent in which the starting materials are sufficiently soluble. It is preferred that a suitable polar organic solvent such as an alcohol, or mixture of alcohols, is used as solvent. It is preferred that the solvent is predominantly methanol, and particularly a mixture of methanol and isopropanol. It is further preferred that the reaction mixture contains a suitable percentage of water, generally less than 10% by volume, such as from about 2% to 10% by volume. It is particularly preferred that the solvent contains about 5% by volume of water. It has been found that the presence of a suitable amount of water provides significant advantages, particularly with regards to inhibiting the conversion of the aldehyde (II) into the undesirable acetal side product (IV).

(IV)

by reaction with the solvent $R^1OH$.

This side reaction, like the primary condensation reaction, is catalysed by acid and thus is promoted along with the primary reaction by the catalytic amounts of acid present in the hydroxylamine feedstock.

Overall solvent compositions (by volume) which are preferred include:

| | |
|---|---|
| methanol | 98 to 70%; |
| isopropanol | 0 to 30%; |
| water | 2 to 10%. |

Especially preferred are:

| | |
|---|---|
| methanol | about 80%; |
| isopropanol | about 15%; |
| water | about 5%. |

The presence of a suitable amount of water in the solvent also significantly improves the kinetics of the process and allows a more concentrated reaction mixture to be used. The proportion of reaction solvent is typically maintained at about 2 to 10 mL of solvent per gram of nitrone product or greater, with proportions of from especially 4 to 8 mL per gram being preferred.

The condensation is conducted at a temperature from about ambient temperature to about 150° C.; good results are achieved at a temperature of from about ambient to about 125° C.; with temperatures of from about 40° C. to about 100° C. being preferred. The condensation reaction is carried out substantially to completion. Usually this takes from about 3 hours to about 24 hours, especially about 3 hours to about 8 hours. Longer times are sometimes favoured since the side reaction to form acetal is reversible and prolonged reaction periods drive the equilibrium toward the desired product (I).

Isolation

The isolation of the product of formula (I) formed in the above condensation may be achieved by using standard techniques that are well known in the art. It is particularly advantageous that the product be isolated using a suitable crystallisation technique. Thus in a typical isolation, on completion of the reaction of the aldehyde (II) with N-tert-butylhydroxylamine (III), the reaction mixture is cooled to ambient temperature and then filtered in order to remove any insoluble material. The filtrate is then heated at reflux and crystallisation is induced by the gradual addition of a suitable crystallisation agent such as isopropanol or ethyl acetate while water and methanol are removed by distillation. The crystallisation agent is typically an organic liquid that is miscible with the reaction solvent but one in which the nitrone product is less soluble. The agent is also generally a volatile material, such as a material having 5 or less carbon atoms. After cooling once more, the solid product is isolated by filtration and dried. The use of isopropanol as a crystallisation agent is particularly preferred.

Alternatively, crystallisation may be induced by the addition of a suitable agent such as isopropanol or ethyl acetate without the filtrate having first been heated. Again, the use of isopropanol is particularly preferred.

The water content of α-(2,4-disulfophenyl)-N-tert-butylnitrone disodium salt obtained using the process of the present invention is dependent on the nature of the methodology used for the isolation of the product and the final drying process that is used. Thus, extensive drying at elevated temperatures and under reduced pressure will yield essentially anhydrous material. Such material is however significantly hygroscopic, forming eventually a trihydrate. Drying of the trihydrate regenerates the anhydrous form. The trihydrate form is obtained directly by crystallisation of α-(2,4-disulfophenyl)-N-tert-butylnitrone disodium salt from hot water, or by passing humidified air over the solid.

Addition of up to about 5% by volume water to the crystallisation agent can push the product toward the hydrated form and decrease the amount of occluded organic liquids in the crystalline product.

Water addition can also have the benefit of decreasing the amount of salt and associated by-products, such as aldehyde starting material incorporated into the isolated product (I).

The invention is illustrated, but is in no way limited, by the following examples:

EXAMPLE 1

The synthesis of α-(2,4-disulfophenyl)-N-tert-butylnitrone disodium salt using an isopropanol/methanol premix, condensation reaction, isopropanol distillation, water adjustment, filtration and drying process Sodium methoxide (1012 g) in isopropanol (1.4 L) and methanol (0.36 L) was added to N-tert-butyl-hydroxylamine hydrochloride (2340.3 g) in methanol (1.80 L) and isopropanol (7.5 L), then stirred for 40 minutes. The mixture was filtered and the filtrate then added to a suspension of 4-formyl-1,3-benzenedisulfonic acid disodium salt (4500 g) in methanol (32.0 L) and water (2.10 L) in a 50 L jacketed reactor fitted with reflux condenser and overhead stirrer. The mixture was refluxed for 8 hours to give a solution that was then transferred by peristaltic pump through an in-line filter. The mixture was distilled at such a rate so as to maintain an approximately constant volume while isopropanol:water (99:1) was added. A total of 40 L distillate was collected and 40 L isopropanol:water (99:1) added. The resulting suspension was cooled to 25.2° C. Water (1200 mL) was added and the mixture was stirred for 1.8 hours, then filtered. The white solid was washed with isopropanol (2×8.0 L) then dried in two portions in a fluid bed dryer at 100° C. to give the required product (4183.7 g, 86.8%).

EXAMPLE 2

The synthesis of α-(2,4-disulfophenyl)-N-tert-butylnitrone disodium salt using a 100% methanol premix, condensation reaction, distillation, water adjustment, filtration and drying process Sodium methoxide (186.3 g, 3.45 equiv.) in methanol (2.66 L) was added to N-tert-butylhydroxylamine hydrochloride (461.3 g, 3.65 equiv.) in methanol (2.3 L). An additional 1.15 L of methanol was added and the mixture then stirred for 20 minutes. The mixture was filtered and the filtrate added to a suspension of 4-formyl-1,3-benzenedisulfonic acid disodium salt (1000 g) in methanol (2.65 L) and water (0.45 L) in a 12 L jacketed reactor fitted with reflux condenser and overhead stirrer. The mixture was refluxed for 6 hours to give a solution which was then transferred by peristaltic pump through an in-line filter into a 12 L jacketed vessel, fitted for distillation with a stillhead adapter, condenser and overhead stirrer. The mixture was distilled at such a rate so as to maintain an approximately constant volume while isopropanol:water (99:1) was added. A total of 9 L distillate was collected and 9 L isopropanol:water (99:1) added. The suspension was cooled to ambient temperature. Water (600 mL) was added and the mixture stirred for 2 hours and 20 minutes, then filtered. The white solid was washed with isopropanol (1×800 mL), then dried in a fluid bed dryer at 100° C. for about one hour to give 568 g of the required product (47.2% yield).

HPLC (% area): 99.3% α-(2,4-disulfophenyl)-N-tert-butylnitrone disodium salt; 0.13% 4-formyl-1,3-benzenedisulfonic acid disodium salt; 0.05% 4-formyl-1,3-benzenedisulfonic acid disodium salt dimethyl acetal.

EXAMPLE 3

Preparation of α-(2,4-disulfophenyl)-N-tert-butylnitrone disodium salt using an 100% isopropanol premix, condensation reaction, ethyl acetate distillation, water adjustment, filtration and drying process Sodium methoxide (156.8 g, 2.90 equiv.) in isopropanol (0.5 L) was added to N-tert-butylhydroxylamine hydrochloride (379.2 g, 3.0 equiv.) in isopropanol (2.45 L), then stirred for 20 minutes. The mixture was filtered and the solid then washed with isopropanol (0.5 L). The filtrate and washings were added to a suspension of 4-formyl-1,3-benzenedisulfonic acid disodium salt (814.5 g) in methanol (7.36 L) and water (0.49 L) in a 12 L jacketed reactor fitted with reflux condenser and overhead stirrer. After 7.5 hours reflux, an additional amount of sodium methoxide (15.6 g) in isopropanol (245 mL) was added to N-tert-butylhydroxylamine hydrochloride (37.9 g) in isopropanol (50 mL), mixed and filtered and the filtrate added to the reaction reflux and reflux continued a further 4 hours. The reaction was cooled and sodium methoxide (12.0 g) was added and the reaction mixture then stirred for 20 minutes. The solution was then transferred using a peristaltic pump through an in-line filter into a 12 L jacketed vessel, fitted for distillation with a stillhead adapter, condenser and an overhead stirrer. The mixture was distilled at such a rate to maintain an approximately constant volume while isopropanol: water (99:1) was added. A total of 10 L of distillate was collected and 10 L of isopropanol: water (99:1) was added. The suspension was cooled to ambient temperature. Water (400 mL) was added and the mixture was stirred, then filtered. The white solid was washed with isopropanol (2×200 mL) then dried in a fluid bed dryer at 100° C. for about one hour to give the required product (86% yield). HPLC (% area): 98.3% α-(2,4-disulfophenyl)-N-tert-butylnitrone disodium salt; 0.30% 4-formyl-1,3-benzenedisulfonic acid disodium salt; 0.70% 4-formyl-1,3-benzenedisulfonic acid disodium salt dimethyl acetal; chloride (ISE, w/w): 0.68%.

EXAMPLE 4

In a 50 L reactor, methanol (32.0 L), water (2.10 L) and 4-formyl-1,3-benzenedisulfonic acid disodium salt (4500.7 g) were stirred and heated at 75° C. while N-tert-butylhydroxylamine [prepared by treating N-tert-butylhydroxylamine hydrochloride (2340.7 g, 18.96 moles) in isopropanol (7.50 L) with sodium methoxide (1012.3 g, 18.74 moles) in isopropanol (3.20 L) and methanol (0.36 L), then removing the sodium chloride by-product by filtration] was added. Additional N-tert-butylhydroxylamine [prepared from treating N-tert-butylhydroxylamine hydrochloride (234.0 g) with sodium methoxide (95.0 g) in isopropanol and methanol (880 mL and 180 mL respectively)] was added after 6 hours reflux. After a total of 11 hours reflux the reaction was complete. The mixture was filtered into a second reactor, sodium methoxide (24.5 g) added, the mixture was heated to distillation and then isopropanol: water (99:1) was added at the same rate at which the distillate was removed. The total distillation time was 24 hours. Water (1200 mL) was added to the stirred suspension, which after cooling to <30° C. was filtered, washed with isopropanol (2×8 L) and dried in a fluid bed dryer to give the required product in 91.7% yield.

What is claimed is:

1. A process for the preparation of a compound of general formula (I)

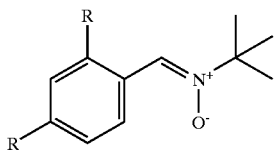

wherein each R independently represents $SO_3H$ or a salt thereof, which process comprises:
   a) incompletely neutralising a N-tert-butylhydroxylamine acid addition salt in a solvent comprising at least one alcohol using between 0.9 to 1.0 equivalents of a base;
   b) removing the inorganic salt by-product of step (a);
   c) admixing the resulting solution from step (b) with an aldehyde of general formula (II)

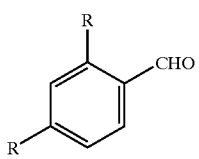

wherein R is as defined above, thereby forming a condensation product comprising compound (I); and
   d) isolating compound (I) from the condensation product.

2. A process according to claim 1 wherein R represents $SO_3^-Na^+$.

3. A process according to claim 1 wherein 0.95 to 0.99 equivalents of base are used in step (a).

4. A process according to claim 1 wherein the solvent in step (a) comprises, by volume, 10 to 35% methanol and 65 to 90% isopropanol.

5. A process according to claim 1 wherein solvent for the condensation with the aldehyde (II) comprises, by volume, 70 to 98% methanol; 0 to 30% isopropanol: and 2 to 10% water.

6. A process according to claim 1 wherein the N-tert-butylhydroxylamine acid addition salt is N-tert-butylhydroxylamine hydrochloride.

7. A process according to claim 1 wherein the base used in step (a) is sodium methoxide.

8. A process according to claim 6 wherein, in step (b), the sodium chloride is removed by filtration.

* * * * *